United States Patent
Trail et al.

(10) Patent No.: US 11,478,664 B2
(45) Date of Patent: Oct. 25, 2022

(54) PARTICLE BEAM GUN CONTROL SYSTEMS AND METHODS

(71) Applicant: Varian Medical Systems, Inc., Palo Alto, CA (US)

(72) Inventors: Mark Everett Trail, Menlo Park, CA (US); James Edward Clayton, San jose, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 16/920,019

(22) Filed: Jul. 2, 2020

(65) Prior Publication Data
US 2020/0330798 A1 Oct. 22, 2020

Related U.S. Application Data

(62) Division of application No. 15/657,036, filed on Jul. 21, 2017, now Pat. No. 10,843,011.

(51) Int. Cl.
*A61L 2/10* (2006.01)
*A61N 5/10* (2006.01)
(Continued)

(52) U.S. Cl.
CPC ............. *A61N 5/1077* (2013.01); *A61N 5/10* (2013.01); *H01J 35/065* (2013.01); *H01J 35/14* (2013.01);
(Continued)

(58) Field of Classification Search
CPC .......... A61N 2005/1085; A61N 5/1081; A61N 5/1077; A61N 5/10; H01J 35/14; H01J 35/065; H01J 37/1472; H01J 3/025
See application file for complete search history.

(56) References Cited

U.S. PATENT DOCUMENTS

| 4,163,901 A | 8/1979 | Azam |
| 4,737,680 A * | 4/1988 | True ...................... H01J 23/065 313/449 |

(Continued)

FOREIGN PATENT DOCUMENTS

| CN | 104001270 | 8/2014 |
| CN | 106730407 | 5/2017 |

(Continued)

OTHER PUBLICATIONS http://hyperphysics.phy-astr.gsu.edu/hbase/mod2.html, retrieved Mar. 8, 2022. (Year: 2022).*

(Continued)

*Primary Examiner* — Wyatt A Stoffa

(57) ABSTRACT

Presented systems and methods facilitate efficient and effective monitoring of particle beams. In some embodiments, a radiation gun system comprises: a particle beam gun that generates a particle beam, and a gun control component that controls the gun particle beam generation characteristics, including particle beam fidelity characteristics. The particle beam characteristics can be compatible with FLASH radiation therapy. Resolution control of the particle beam generation can enable dose delivery at an intra-pulse level and micro-bunch level. The micro-bunch can include individual bunches per each 3 GHz RF cycle within the 5 to 15 μsec pulse-width. The FLASH radiation therapy dose delivery can have a bunch level resolution of approximately $4.4 \times 10^{-6}$ cGy/bunch.

13 Claims, 5 Drawing Sheets

(51) Int. Cl.
*H01J 37/073* (2006.01)
*H01J 35/14* (2006.01)
*H01J 35/06* (2006.01)
*H01J 37/075* (2006.01)
*H05H 9/00* (2006.01)
*H01J 3/02* (2006.01)
*H01J 37/147* (2006.01)

(52) U.S. Cl.
CPC .......... *H01J 37/073* (2013.01); *H01J 37/075* (2013.01); *H05H 9/00* (2013.01); *A61N 5/1081* (2013.01); *A61N 2005/1085* (2013.01); *A61N 2005/1088* (2013.01); *H01J 3/025* (2013.01); *H01J 37/1472* (2013.01)

(56) References Cited

U.S. PATENT DOCUMENTS

| | | | |
|---|---|---|---|
| 4,914,681 A | 4/1990 | Klingenbeck et al. | |
| 4,998,073 A * | 3/1991 | Miyata | H05H 7/06 315/500 |
| 5,153,900 A | 10/1992 | Nomikos et al. | |
| 5,267,294 A | 11/1993 | Kuroda | |
| 5,550,378 A | 8/1996 | Skillicorn et al. | |
| 5,610,967 A | 3/1997 | Moorman et al. | |
| 5,625,663 A | 4/1997 | Swerdloff et al. | |
| 5,682,412 A | 10/1997 | Skillicorn et al. | |
| 5,757,885 A | 5/1998 | Yao et al. | |
| 5,834,787 A | 11/1998 | Bunker | |
| 6,198,802 B1 | 3/2001 | Elliott et al. | |
| 6,222,544 B1 | 4/2001 | Tarr et al. | |
| 6,234,671 B1 | 5/2001 | Solomon et al. | |
| 6,260,005 B1 | 7/2001 | Yang et al. | |
| 6,379,380 B1 | 4/2002 | Satz | |
| 6,411,675 B1 | 6/2002 | Llacer | |
| 6,445,766 B1 | 9/2002 | Whitham | |
| 6,504,899 B2 | 1/2003 | Pugachev et al. | |
| 6,580,084 B1 | 6/2003 | Hiramoto et al. | |
| 6,580,940 B2 | 6/2003 | Gutman | |
| 6,888,832 B2 | 5/2005 | Richardson et al. | |
| 6,920,202 B1 | 7/2005 | Dinsmore | |
| 6,993,112 B2 | 1/2006 | Hesse | |
| 7,268,358 B2 | 9/2007 | Ma et al. | |
| 7,423,278 B2 | 9/2008 | Amaldi et al. | |
| 7,453,983 B2 | 11/2008 | Schildkraut et al. | |
| 7,515,681 B2 | 4/2009 | Ebstein | |
| 7,522,706 B2 | 4/2009 | Lu et al. | |
| 7,554,275 B2 | 6/2009 | Amaldi | |
| 7,560,715 B2 | 7/2009 | Pedroni | |
| 7,590,219 B2 | 9/2009 | Maurer, Jr. et al. | |
| 7,616,735 B2 | 11/2009 | Maciunas et al. | |
| 7,623,623 B2 | 11/2009 | Raanes et al. | |
| 7,778,691 B2 | 8/2010 | Zhang et al. | |
| 7,807,982 B2 | 10/2010 | Nishiuchi et al. | |
| 7,831,289 B2 | 11/2010 | Riker et al. | |
| 7,835,492 B1 | 11/2010 | Sahadevan | |
| 7,907,699 B2 | 3/2011 | Long et al. | |
| 8,071,966 B2 | 12/2011 | Kaiser et al. | |
| 8,121,253 B2 | 2/2012 | Nelms | |
| 8,253,121 B2 | 8/2012 | Gnutzmann et al. | |
| 8,284,898 B2 | 10/2012 | Ho et al. | |
| 8,306,184 B2 | 11/2012 | Chang et al. | |
| 8,401,148 B2 | 3/2013 | Lu et al. | |
| 8,405,056 B2 | 3/2013 | Amaldi et al. | |
| 8,406,844 B2 | 3/2013 | Ruchala et al. | |
| 8,559,596 B2 | 10/2013 | Thomson et al. | |
| 8,600,003 B2 | 12/2013 | Zhou et al. | |
| 8,613,694 B2 | 12/2013 | Walsh | |
| 8,618,521 B2 | 12/2013 | Loo et al. | |
| 8,636,636 B2 | 1/2014 | Shukla et al. | |
| 8,644,571 B1 | 2/2014 | Schulte et al. | |
| 8,699,664 B2 | 4/2014 | Otto et al. | |
| 8,716,663 B2 | 5/2014 | Brusasco et al. | |
| 8,798,343 B2 | 8/2014 | Kabus et al. | |
| 8,836,332 B2 | 9/2014 | Shvartsman et al. | |
| 8,847,179 B2 | 9/2014 | Fujitaka et al. | |
| 8,901,519 B2 | 12/2014 | Schardt et al. | |
| 8,903,471 B2 | 12/2014 | Heid | |
| 8,917,813 B2 | 12/2014 | Maurer, Jr. | |
| 8,948,341 B2 | 2/2015 | Beckman | |
| 8,958,864 B2 | 2/2015 | Amies et al. | |
| 8,983,573 B2 | 3/2015 | Carlone et al. | |
| 8,986,186 B2 | 3/2015 | Zhang et al. | |
| 8,992,404 B2 | 3/2015 | Graf et al. | |
| 8,995,608 B2 | 3/2015 | Zhou et al. | |
| 9,018,603 B2 | 4/2015 | Loo et al. | |
| 9,033,859 B2 | 5/2015 | Fieres et al. | |
| 9,079,027 B2 | 7/2015 | Agano et al. | |
| 9,149,656 B2 | 10/2015 | Tanabe | |
| 9,155,908 B2 | 10/2015 | Meltsner et al. | |
| 9,233,260 B2 | 1/2016 | Slatkin et al. | |
| 9,258,876 B2 | 2/2016 | Cheung et al. | |
| 9,283,406 B2 | 3/2016 | Prieels | |
| 9,308,391 B2 | 4/2016 | Liu et al. | |
| 9,330,879 B2 | 5/2016 | Lewellen et al. | |
| 9,333,374 B2 | 5/2016 | Iwata | |
| 9,468,777 B2 | 10/2016 | Fallone et al. | |
| 9,517,358 B2 | 12/2016 | Velthuis et al. | |
| 9,526,918 B2 | 12/2016 | Kruip | |
| 9,545,444 B2 | 1/2017 | Strober et al. | |
| 9,583,302 B2 | 2/2017 | Figueroa Saavedra et al. | |
| 9,636,381 B2 | 5/2017 | Basile | |
| 9,636,525 B1 | 5/2017 | Sahadevan | |
| 9,649,298 B2 | 5/2017 | Djonov et al. | |
| 9,656,098 B2 | 5/2017 | Goer | |
| 9,694,204 B2 | 7/2017 | Hardemark | |
| 9,776,017 B2 | 10/2017 | Flynn et al. | |
| 9,786,054 B2 | 10/2017 | Taguchi et al. | |
| 9,786,093 B2 | 10/2017 | Svensson | |
| 9,786,465 B2 | 10/2017 | Li et al. | |
| 9,795,806 B2 | 10/2017 | Matsuzaki et al. | |
| 9,801,594 B2 | 10/2017 | Boyd et al. | |
| 9,844,358 B2 | 12/2017 | Wiggers et al. | |
| 9,854,662 B2 | 12/2017 | Mishin | |
| 9,884,206 B2 | 2/2018 | Schulte et al. | |
| 9,931,522 B2 | 4/2018 | Bharadwaj et al. | |
| 9,962,562 B2 | 5/2018 | Fahrig et al. | |
| 9,974,977 B2 | 5/2018 | Lachaine et al. | |
| 9,987,502 B1 | 6/2018 | Gattiker et al. | |
| 10,007,961 B2 | 6/2018 | Grudzinski et al. | |
| 10,022,564 B2 | 7/2018 | Thieme et al. | |
| 10,071,264 B2 | 9/2018 | Liger | |
| 10,080,912 B2 | 9/2018 | Kwak et al. | |
| 10,092,774 B1 | 10/2018 | Vanderstraten et al. | |
| 10,183,179 B1 | 1/2019 | Smith et al. | |
| 10,188,875 B2 | 1/2019 | Kwak et al. | |
| 10,206,871 B2 | 2/2019 | Lin et al. | |
| 10,212,800 B2 | 2/2019 | Agustsson et al. | |
| 10,232,193 B2 | 3/2019 | Iseki | |
| 10,258,810 B2 | 4/2019 | Zwart et al. | |
| 10,272,264 B2 | 4/2019 | Ollila et al. | |
| 10,279,196 B2 | 5/2019 | West et al. | |
| 10,293,184 B2 | 5/2019 | Pishdad et al. | |
| 10,307,614 B2 | 6/2019 | Schnarr | |
| 10,307,615 B2 | 6/2019 | Ollila et al. | |
| 10,315,047 B2 | 6/2019 | Glimelius et al. | |
| 10,413,755 B1 | 9/2019 | Sahadevan | |
| 10,449,389 B2 | 10/2019 | Ollila et al. | |
| 10,485,988 B2 | 11/2019 | Kuusela et al. | |
| 10,525,285 B1 | 1/2020 | Friedman | |
| 10,549,117 B2 | 2/2020 | Vanderstraten et al. | |
| 10,603,514 B2 | 3/2020 | Grittani et al. | |
| 10,609,806 B2 | 3/2020 | Roecken et al. | |
| 10,636,609 B1 | 4/2020 | Bertsche et al. | |
| 10,660,588 B2 | 5/2020 | Boyd et al. | |
| 10,661,100 B2 | 5/2020 | Shen | |
| 10,682,528 B2 | 6/2020 | Ansorge et al. | |
| 10,702,716 B2 | 7/2020 | Heese | |
| 10,758,746 B2 | 9/2020 | Kwak et al. | |
| 10,843,011 B2 * | 11/2020 | Trail | H01J 35/065 |
| 10,870,018 B2 | 12/2020 | Bartkoski et al. | |
| 2002/0030164 A1 | 3/2002 | Akiyama et al. | |
| 2002/0057760 A1 | 5/2002 | Carroll et al. | |
| 2006/0193435 A1 | 8/2006 | Hara et al. | |

(56) References Cited

U.S. PATENT DOCUMENTS

| | | | |
|---|---|---|---|
| 2006/0231775 A1* | 10/2006 | Harada | A61N 5/10 250/492.3 |
| 2006/0274061 A1 | 12/2006 | Wang et al. | |
| 2007/0034812 A1 | 2/2007 | Ma et al. | |
| 2007/0287878 A1 | 12/2007 | Fantini et al. | |
| 2008/0023644 A1 | 1/2008 | Pedroni | |
| 2008/0049897 A1 | 2/2008 | Molloy | |
| 2008/0226030 A1 | 9/2008 | Otto | |
| 2009/0026912 A1* | 1/2009 | Lordi | H01J 37/063 250/492.23 |
| 2009/0063110 A1 | 3/2009 | Failla et al. | |
| 2009/0283702 A1 | 11/2009 | Umezawa et al. | |
| 2009/0287467 A1 | 11/2009 | Sparks et al. | |
| 2010/0003770 A1 | 1/2010 | Shibata et al. | |
| 2010/0119032 A1 | 5/2010 | Yan et al. | |
| 2010/0177870 A1 | 7/2010 | Nord et al. | |
| 2010/0178245 A1 | 7/2010 | Arnsdorf et al. | |
| 2010/0195793 A1 | 8/2010 | Nelms | |
| 2010/0260317 A1 | 10/2010 | Chang et al. | |
| 2010/0288945 A1 | 11/2010 | Gnutzmann et al. | |
| 2010/0327785 A1* | 12/2010 | Crewson | H05H 7/04 335/297 |
| 2011/0006214 A1 | 1/2011 | Bonig | |
| 2011/0006224 A1 | 1/2011 | Maltz et al. | |
| 2011/0091015 A1 | 4/2011 | Yu et al. | |
| 2011/0135058 A1 | 6/2011 | Sgouros et al. | |
| 2011/0168903 A1 | 7/2011 | Kyele et al. | |
| 2012/0076271 A1 | 3/2012 | Yan et al. | |
| 2012/0134470 A1 | 5/2012 | Shibuya et al. | |
| 2012/0136194 A1 | 5/2012 | Zhang et al. | |
| 2012/0157746 A1 | 6/2012 | Meltsner et al. | |
| 2012/0171745 A1 | 7/2012 | Itoh | |
| 2012/0197058 A1 | 8/2012 | Shukla et al. | |
| 2012/0253495 A1 | 10/2012 | Wright et al. | |
| 2013/0116929 A1 | 5/2013 | Carlton et al. | |
| 2013/0150922 A1 | 6/2013 | Butson et al. | |
| 2013/0172658 A1 | 7/2013 | Brahme et al. | |
| 2013/0177641 A1 | 7/2013 | Ghoroghchian | |
| 2013/0231516 A1* | 9/2013 | Loo | A61N 5/1064 600/1 |
| 2014/0152176 A1* | 6/2014 | Chang | H01J 25/10 315/14 |
| 2014/0177807 A1 | 6/2014 | Lewellen et al. | |
| 2014/0185776 A1 | 7/2014 | Li et al. | |
| 2014/0206926 A1 | 7/2014 | van der Laarse | |
| 2014/0265823 A1 | 9/2014 | Boisseau et al. | |
| 2014/0270086 A1 | 9/2014 | Krasnykh | |
| 2014/0275706 A1 | 9/2014 | Dean et al. | |
| 2014/0369476 A1 | 12/2014 | Harding | |
| 2015/0011817 A1 | 1/2015 | Feng | |
| 2015/0057484 A1 | 2/2015 | Amaldi | |
| 2015/0087882 A1 | 3/2015 | Pausch et al. | |
| 2015/0094838 A1 | 4/2015 | MacLaverty | |
| 2015/0117616 A1 | 4/2015 | Ishii et al. | |
| 2015/0202464 A1 | 7/2015 | Brand et al. | |
| 2015/0306423 A1 | 10/2015 | Bharat et al. | |
| 2016/0193482 A1 | 7/2016 | Fahrig et al. | |
| 2016/0225477 A1 | 8/2016 | Banine et al. | |
| 2016/0279444 A1 | 9/2016 | Schlosser | |
| 2016/0287905 A1 | 10/2016 | Liger | |
| 2016/0310764 A1 | 10/2016 | Bharadwaj et al. | |
| 2017/0028220 A1 | 2/2017 | Schulte et al. | |
| 2017/0189721 A1 | 7/2017 | Sumanaweera et al. | |
| 2017/0203125 A1 | 7/2017 | Amato et al. | |
| 2017/0203129 A1 | 7/2017 | Dessy | |
| 2017/0281973 A1 | 10/2017 | Allen et al. | |
| 2018/0021594 A1 | 1/2018 | Papp et al. | |
| 2018/0043183 A1 | 2/2018 | Sheng et al. | |
| 2018/0056090 A1 | 3/2018 | Jordan et al. | |
| 2018/0099154 A1 | 4/2018 | Prieels | |
| 2018/0099155 A1 | 4/2018 | Prieels et al. | |
| 2018/0099159 A1 | 4/2018 | Forton et al. | |
| 2018/0154183 A1 | 6/2018 | Sahadevan | |
| 2018/0197303 A1 | 7/2018 | Jordan et al. | |
| 2018/0207425 A1 | 7/2018 | Carlton et al. | |
| 2018/0235554 A1 | 8/2018 | Burgett | |
| 2018/0236268 A1 | 8/2018 | Zwart et al. | |
| 2019/0022407 A1 | 1/2019 | Abel et al. | |
| 2019/0022422 A1 | 1/2019 | Trail et al. | |
| 2019/0054315 A1 | 2/2019 | Isola et al. | |
| 2019/0070435 A1 | 3/2019 | Joe Anto et al. | |
| 2019/0168027 A1 | 6/2019 | Smith et al. | |
| 2019/0255361 A1 | 8/2019 | Mansfield | |
| 2019/0299027 A1 | 10/2019 | Fujii et al. | |
| 2019/0299029 A1 | 10/2019 | Inoue | |
| 2019/0351259 A1 | 11/2019 | Lee et al. | |
| 2020/0001118 A1 | 1/2020 | Snider, III et al. | |
| 2020/0022248 A1 | 1/2020 | Yi et al. | |
| 2020/0030633 A1 | 1/2020 | Van Heteren et al. | |
| 2020/0035438 A1 | 1/2020 | Star-Lack et al. | |
| 2020/0069818 A1 | 3/2020 | Jaskula-Ranga et al. | |
| 2020/0164224 A1 | 5/2020 | Vanderstraten et al. | |
| 2020/0178890 A1 | 6/2020 | Otto | |
| 2020/0197730 A1 | 6/2020 | Safavi-Naeini et al. | |
| 2020/0254279 A1 | 8/2020 | Ohishi | |
| 2020/0269068 A1 | 8/2020 | Abel et al. | |
| 2020/0276456 A1 | 9/2020 | Swerdloff | |
| 2020/0282234 A1 | 9/2020 | Folkerts et al. | |
| 2021/0220674 A1* | 7/2021 | Purwar | A61N 5/1044 |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 2108401 A1 | 11/2008 |
| EP | 2810693 A2 | 10/2014 |
| EP | 2805745 | 11/2014 |
| EP | 2979728 | 2/2016 |
| EP | 3043863 A4 | 7/2016 |
| EP | 3103519 A1 | 12/2016 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2014-161706 A | 9/2014 |
| JP | 2017-098000 A | 6/2017 |
| JP | 2019097969 | 6/2019 |
| WO | 2006005059 | 12/2006 |
| WO | 2007017177 | 2/2007 |
| WO | 2009042952 A1 | 4/2009 |
| WO | 2010018476 | 2/2010 |
| WO | 2010088442 A1 | 8/2010 |
| WO | 2012135196 A1 | 10/2012 |
| WO | 2013038240 A1 | 3/2013 |
| WO | 2013081218 | 6/2013 |
| WO | 2013133936 | 9/2013 |
| WO | 2014139493 | 9/2014 |
| WO | 2015038832 | 3/2015 |
| WO | 2015038832 A1 | 3/2015 |
| WO | 2015077881 A1 | 4/2015 |
| WO | 2015102680 | 7/2015 |
| WO | 2015153746 A1 | 10/2015 |
| WO | 2016094284 A1 | 6/2016 |
| WO | 2016094284 A9 | 6/2016 |
| WO | 2016122957 | 8/2016 |
| WO | 2017156316 | 9/2017 |
| WO | 2017173443 A1 | 10/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |

(56) References Cited

FOREIGN PATENT DOCUMENTS

| WO | 2020064832 | 4/2020 |
|---|---|---|
| WO | 2020107121 | 6/2020 |
| WO | 2020159360 | 8/2020 |

OTHER PUBLICATIONS

Wen C. His, Michael F. Moyers, Dmitri Nichporov, Vladimir Anferov, Mark Wolanski, Chris E. Allgower, Jonathan B. Farr, Anthony E. Mascia, Andreis N. Schreuder, "Energy spectrum control for modulated proton beams", Medical Physics, (2009) 36(6) 2297-2308, http://www.ncbi.nlm.nih.gov/pmc/articles/PMC2832068/.

V. Anferov, M. Ball, G.P. Berg, B. Broderick, J. Collins, G. East, D. Friesel, D. Jenner, W.P. Jones, J. Katuin, S. Klein, C. Nelson, N. Schreuder, Wm. Starks, J. Self, "The Indiana University Midwest Proton Radiation Institute", Proceedings of the 2001 Particle Accelerator Conference, (2001) p. 645-64 https://accelconf.web.cern.ch/accelconf/p01/PAPERS/FOAA004.PDF.

Th. Haberer,W. Becher,D. Schardt,G. Kraft "Magnetic scanning system for heavy ion therapy" Nuclear Instruments and Methods in Physics Research Section A: Accelerators, Spectrometers, Detectors and Associated Equipment, NIM , Elsevie, Jun. 10, 1993, vol. 330, Issues 1-2, Jun. 10, 1993, pp. 296-305.

Amaldi, Tera Foundation, Novara, Italy A. Degiovanni, Cern, Geneva, Switzerland Linac 2014. Proton and Carbon Linacs for Hadron Therapy U. http://accelconf.web.cern.ch/AccelConf/LINAC2014/papers/friob02.pdf.

Montay-Gruel P, Petersson K, Jaccard M, Boivin G, Germond JF, Petit B, Doenlen R, Favaudon V, Bochud F, Bailat C, Bourhis J, Vozenin MC. Irradiation in a flash: Unique sparing of memory in mice after whole brain irradiation with dose rates above 100Gy/s. Radiother Oncol. May 22, 2017. pii: S0167-8140(17)30365-1. doi: 10.1016/j.radonc.2017.05.003. [Epub ahead of print] PubMed PMID: 28545957.

Favaudon V, Caplier L, Monceau V, Pouzoulet F, Sayarath M, Fouillade C, Poupon Mf, Brito I, Hupe P, Bourhis J, Hall J, Fontaine JJ, Vozenin MC. Ultrahigh dose-rate Flash irradiation increases the differential response between normal and tumor tissue in mice. Sci Transl Med. Jul. 16, 2014;6(245):2451a93. doi: 10.1126/scitranslmed. 3008973. PubMed PMID:25031268.

Loo BW, Schuler E, Lartey FM, Rafat M, King GJ, Trovati S, Koong AC, Maxim PG. Delivery of Ultra-Rapid Flash Radiation Therapy and Demonstration of Normal Tissue Sparing After Abdominal Irradiation of Mice. International Journal of Radiation Oncology Biology Physics, vol. 98 Issue: 2 pp. E16-E16 Supplement: S Meeting Abstract: P003 Published: Jun. 1, 2017.

M Bopp, H. Fitze, P. Sigg, and L Stingelin "Upgrade concepts of the PSI accelerator RF systems for a projected 3 mA operation" , Citation: AIP Conference Proceedings 600, 300 (2001); doi: 10.1063/1.1435259.

K. Peach, et al. "Pamela—A Model for an FFAG Based Hadron Therapy Machine", Proceedings of PAC07, Albuquerque, New Mexico, USA, 2007, pp. 2880-2882.

S. Benedetti, A. Grudiev, and A. Latina Phys. Rev. Accel. Beams 20, 040101—Published Apr. 13, 2017.

Valery Dolgashev, Sami Tantawi, Yasuo Higashi, Bruno Spataro, "Geometric dependence of radio-frequency breakdown in normal conducting accelerating structures," Applied Physics Letters, vol. 97, Issue 17, pp. 171501-171501-3, Oct. 2010.

Lisa Laurent, Sami Tantawi, Valery Dolgashev, Chris Nantista, Yasuo Higashi, Markus Aicheler, Samuli Heikkinen, and Walter Wuensch, Experimental Study of RF Pulsed Heating Phys. Rev. ST Accel. Beams 14, 041001 (2011) [21 pages].

S. Tantawi, Z. Li, patent pending, Title: "Distributed Coupling and Multi-Frequency Microwave Accelerators", Filed: Jul. 9, 2014, U.S. Appl. No. 62/022,469.

S. Tantawi, M.Nasr, "Designs and High Power Tests of Distributed Coupling Linacs" IFIC, Jun. 13-16, 2017 , Valencia , Spainhttps://indico.cern.ch/event/589548/contributions/2615455/attachments/1479738/2294080/Mamdouh_High_Gradient_2017.pdf.

Jensen, Aaron, Jeff Neilson, and Sami Tantawi. "X-band multi-beam klystron design and progress report." Vacuum Electronics Conference (IVEC), 2015 IEEE International. IEEE, 2015.

K.Halbach, "Design of permanent multipole magnets with oriented rare earth cobalt material", Nuclear Instruments and Methods , vol. 169, Issue 1, Feb. 1, 1980, pp. 1-10 [http://www.sciencedirect.com/science/article/pii/0029554X80900944].

J. K. Lim, P. Frigola, G. Travish, J. B. Rosenzweig, S. G. Anderson, W. J. Brown, J. S. Jacob, C. L. Robbins, and A. M. Tremaine, "Adjustable, short focal length permanent-magnet quadrupole based electron beam final focus system" Phys. Rev. ST Accel. Beams 8, 072401—Published Jul. 15, 2005.

Sayyed Bijan Jiaa, Mohammad Hadi Hadizadeha, Ali Asghar Mowlavi,Mandy Ebrahimi Loushab "Evaluation of energy deposition and secondary particle production in proton therapy of brain using a slab head phantom" Elsevier, Reports of Practical Oncology & Radiotherapy,vol. 19, Issue 6, Nov.-Dec. 2014, pp. 376-384.

J.Perl, J Shin, J Schumann, B Faddegon and H Paganetti, "TOPAS—An innovative proton Monte Carlo platform for research and clinical applications," Med. Phys. 39:6818-6837, 2012, PMID: 23127075, PMID: 23127075.

Lisa Polster, Jan Schuemann, Ilaria Rinaldi, Lucas Burigo, Aimee Louise McNamara, Robert D Stewart, Andrea Attili, David J. Carlson, Alejandro Carabe-Fernadez, Bruce Faddegon, Joseph Perl, and Harald Paganetti, "Extension of TOPAS for the simulation of proton radiation on molecular and cellular endpoints," Phys Med Biol Jun. 10, 2015;60 (13):5053-5070, PMID: 26061583.

Vladimir A. Bashkirov a,n , Robert P. Johnson b , Hartmut F.-W. Sadrozinski b , Reinhard W. Schulte a "Development of proton computed tomography detectors for applications in hadron therapy", NIM Nuclear Instruments and Methods in Physics Research A ( under press a the time of writing proposal) http://www.sciencedirect.com/science/article/pii/S0168900215009274 (abstract), Feb. 11, 2016.

Qiyong Fan, Akshay Nanduri, Samuel Mazin, Lei Zhu, "Emission guided radiation therapy for lung and prostate cancers: A feasibility study on a digital patient", Med. Phys. 39 (11), Nov. 2012, 0094-2405/2012/39(11)/7140/13, 13 pages.

Vincent Favuadon, Laura Caplier, Virginie Monceau, Frederic Pouzoulet, Mano Sayarath, Charles Fouillade, Marie-France Poupon, Isabel Brito, Philippe Hupe, Jean Bounhis, Janet Hall, Jean-Jacques Fontaine, Marie-Catherine Vozenin, vol. 6 Issue 245 245ra93, www.ScienceTranslationalMedicine.org, UltraHigh dose-rate FLASH irradiation increase4s the differential response between normal and tumor tissue in mice, 9 pages, Jul. 16, 2014.

Radiotherapy "flashes" to reduce side effects, An effect for each mode of administration, Images of tissue sections, Ultra-high dose-rate, Science Translational Medicine, Jul. 16, 2014, 3 pages.

To introduce the concept of pseudo beam's-eye-view (pBEV), to establish a framework for computer-assisted beam orientation selection in intensity-modulated radiation therapy(IMRT), and to evaluate the utility of the proposed techniquie, Dec. 1, 2001 vol. 51, Issue 5, 3 pages, Pseudo beam's-eye-view as applied to beam orientation selection in intensity-modulated radiation therapy.

U. Amaldi et al., "Cyclinacs: Fast-Cycling Accelerators for Hadrontherapy," Nuclear Inst. and Methods in Physics Research, Mar. 2009.

S. Verdu-Andres et al., "CABOTO, a high-gradient linac for hadrontherapy," Journal of Radiation Research, 2013, 54, pp. i155-i161.

A. Degiovanni et al., "Design of a Fast-Cycling High-Gradient Rotating Linac for Protontherapy," Proceedings of IPAC2013, Shanghai, China, THPWA008, 2013, pp. 3642-3644.

S. Verdu-Andres et al., "Feasibility Study of a High-Gradient Linac for Hadrontherapy," Proceedings of IPAC2011, San Sebastian, Spain, WEPS045, 2011, pp. 2589-2591.

H. Paganetti et al., "Proton Beam Radiotherapy—The State of the Art," New Technologies in Radiation Oncology (Medical Radiation Series), Springer Verlag, Heidelberg, ISBN 3-540-00321-5, Oct. 2005, 36 pages.

(56) References Cited

OTHER PUBLICATIONS

Z. Li, et al., Normal conducting cw transverse crab cavity for producing short pulses in spear3, Proceedings of IPAC2017, Copenhagen, Denmark, 2017, pp. 2840-2843.

Schuler, Emil, et al. "Experimental platform for ultra-high does rate FLASH irradiation of small animals using a clinical linear accelerator." International Journal of Radiation Oncology*Biology*Physics, vol. 97, No. 1, 2017, pp. 195-203.

Valerie Devillaine, Radiotherapy and radiation biology, Radiotherapy—new treatment methods, Radio-toxicity, radio resistance and pediatric cancers, Photo-sensitization and retinoblastoma, 6 pages.

Harris, J.R., et al., "Longitudinal density modulation and energy conversion in intense beams," Physical Review E 76, 026402, The American Physical Society, 2007.

Chang, Sha, "Compensator-intensity-modulated Radiotherapy—A traditional tool for modern application," US Oncological Disease 115 (2006): 1-4 (Year: 2006).

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/S41598-020-65819-y.

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNldmllci5jb20vY29udGVudC9hcnRpY2xlL3BpaS9zMDE2Nz gxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/doi: 10.1118/1.4761951.

Favaudon et al., "Ultrahigh dose-rate, "flash" irradiation minimizes the side-effects of radiotherapy," Cancer / Radiotherapy, vol. 19, Issues 6-7, Oct. 2015, pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects of High Energy Radiation and Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.

Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.0rg/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.

A. J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for eady and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng-pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

(56) References Cited

OTHER PUBLICATIONS

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259 bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J. Groen, "FLASH optimisation in clinical IMPT treatment planning," MSc Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/Published in final edited form as: Med Phys. Apr. 2018; 45(4): 1338-1350. Published online Mar. 1, 2018. doi: 10.1002/mp.12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift für Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.

Harald Paganetti, "Proton Beam Therapy," Jan. 2017, Physics World Discovery, IOP Publishing Ltd, Bristol, UK, 34 pages, DOI: 10.1088/978-0-7503-1370-4.

Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.

Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.

Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.

R. M. De Kruijff, "Flash radiotherapy: ultra-high dose rates to spare healthy tissue," International Journal of Radiation Biology, 2020, vol. 96, No. 4, pp. 419-423, published online: Dec. 19, 2019, https://do.org/10.1080/09553002.2020.1704912.

Mevion Medical Systems, "Focus On The Future: Flash Therapy," Press Releases, Sep. 16, 2019, https://www.mevion.com/newsroom/press-releases/focus-future-flash-therapy.

Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.

David P. Gierga, "Is Flash Radiotherapy coming?", International Organization for Medical Physics, 2020, https://www.iomp.org/iomp-news2-flash-radiotherapy/.

Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.

Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.

Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.

Aetna Inc., "Proton Beam, Neutron Beam, and Carbon Ion Radiotherapy," 2020, No. 0270, http://www.aetna.com/cpb/medical/data/200_299/0270.html.

Nicholas W. Colangelo et al., "The Importance and Clinical Implications of FLASH Ultra-High Dose-Rate Studies or Proton and Heavy Ion Radiotherapy," Radiat Res. Author manuscript; available in PMC Jan. 1, 2021 https://www.ncbi.nlm.nih.gov/pmc/articles/PMC6949397/Published in final edited form as: Radiat Res. Jan. 2020; 193(1): 1-4. Published online Oct. 28, 2019 doi: 10.1667/RR15537.1.

Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.

"FlashRad: Ultra-high dose-rate FLASH radiotherapy to minimize the complications of radiotherapy," 2014, https://siric.curie.fr/sites/default/files/atoms/files/flashrad.pdf.

Tami Freeman, "Flash radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.

(56) References Cited

OTHER PUBLICATIONS

IntraOp Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019.04.001.

Efstathios Kamperis et al., "A Flash back to radiotherapy's past and then fast forward to the future," J Cancer Prev Curr Res. 2019;10(6):142-144. published Nov. 13, 2019, DOI: 10.15406/jcpcr.2019.10.00407.

P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.

Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.

Bazalova-carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.

Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/Published in final edited form as: Radiother Oncol. Oct. 2019; 139: 51-55. Bublished online Mar. 5, 2019. doi: 10.1016/j.radonc 2019.02.009.

N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.0rg/10.1016/j.ijrobp.2019.06.187.

Inserm Press Office, "Radiotherapy 'flashes' to reduce side effects," Press Release, Jul. 16, 2014, https://presse.inserm.fr/en/radiotherapy-flashes-to-reduce-side-effects/13394/.

Eric S. Diffenderfer et al., "Design, Implementation, and in Vivo Validation of a Novel Proton FLASH Radiation fherapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.

Valerie Devillaine, "Radiotherapy and Radiation Biology," Institut Curie, Apr. 21, 2017, https://institut-curie.org/page/radiotherapy-and-radiation-biology.

Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.

Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

Marco Durante et al., "Faster and safer? FLASH ultra-high dose rate in radiotherapy," Br J Radiol 2018; 91(1082):20170628, British Institute of Radiology, Published Online: Dec. 15, 2017, https://doi.org/10.1259/bjr.20170628.

John R. Fischer, "PMB launches FLASH radiotherapy system for use in clinical trials," Healthcare Business News, Jun. 29, 2020, DOTmed.com, Inc., https://www.dotmed.com/news/story/51662.

Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432.CCR-17-3375.full.pdf.

\* cited by examiner

PARTICLE BEAM GUN CONTROL SYSTEMS AND METHODS

RELATED APPLICATIONS

This Application is a divisional that claims the benefit of and priority to U.S. application Ser. No. 15/657,036, filed on Jul. 21, 2017, and entitled "Particle Beam Gun Control Systems and Methods", which is incorporated herein by reference.

FIELD OF THE INVENTION

The present invention relates to the field of particle beam radiation. In some embodiments, radiation systems and methods facilitate fast and effective generation of particle beams.

BACKGROUND

Particle beam radiation can be utilized in a number of different applications and accurately applying an appropriate amount of radiation can be very important. It is often critical to apply an accurate dose of particle beam radiation in medical therapy applications. Particle beam radiation therapy typically includes directing a beam of particles (e.g., ionizing particles, protons, etc.) at an area of tissue. The particles are usually associated with or include a charge. The particles are typically used to stop the growth or spread of the targeted tissue cells by killing them or degrading their cell division ability. While particle beam radiation is generally considered beneficial, there can be a number of potential side effects. The side effects can include unintended damage to DNA of healthy tissue cells. The effectiveness of particle beam radiation is primarily a function of the dose or amount of charged particles that is applied to cancerous cells while avoiding impacts to healthy cells.

The amount of charged particles that are applied to the tissue is typically a function of a dose rate or "current" of charged particles and time the targeted tissue is exposed to the radiation. Faster dose rates usually enable shorter exposure times and that can have a number of benefits, including less opportunity for extraneous events to influence the therapy, increased productivity, and greater convenience to the patient. One approach includes an ultra-high dose rate treatment or modality referred to as FLASH radiotherapy. Therapeutic windows associated with FLASH therapy often enable reduced normal tissue toxicity while maintaining cancerous tissue tumor control. However, these therapeutic windows are usually very narrow or precise and exposure outside the windows can be very detrimental to otherwise healthy tissue. Developing systems and methods to deliver dose rates typically associated with FLASH therapies can be difficult and problematic. Conventional attempts with pulse dropping and servoing are usually too coarse and cannot provide adequate resolution and fidelity.

SUMMARY

Presented systems and methods facilitate efficient and effective generation of particle beams. In some embodiments, a radiation method comprises: generating a particle beam, controlling generation characteristics of the particle beam, accelerating particles in the particle beam; and bending the particle beam along a path directed towards a target. Controlling generation characteristics of the particle beam can include controlling pulsing or gating on and off of the particle beam in accordance with beam fidelity characteristics corresponding to a treatment plan. In one embodiment, the treatment plan includes a dose rate of at least 20 Gy/second. Resolution control of the particle beam generation can enable dose delivery at an intra-pulse level.

In one embodiment, resolution control of the particle beam generation enables dose delivery at a micro-bunch level. The micro-bunch level can include individual bunches per each 3 GHz frequency cycle within a 5 to 15 µsec pulse-width. The generation characteristics of the particle beam can include configuring particles in electron bunches with a bunch level resolution of approximately $4.4 \times 10^{-6}$ cGy/electron bunch, plus or minus 5 percent. In one exemplary 5 µsec pulse there are plus or minus 5 percent of 15,000 pulses or on and off operations/bunch that control a dose output corresponding to a resolution of dose per bunch. In one embodiment, the pulsing or gating is initiated within a middle portion of the pulse reducing energy spread associated with transients of the pulse rise/fall times. The pulsing or gating can occur at a rate that corresponds to a bunch resolution, wherein the bunch resolution defines an amount of electrons in a bunch, and an amount of particles in the particle beam corresponds to the bunch resolution. In one exemplary implementation, the gating is at a rate of 333 psec. The particle beam can include photons or electrons and the target can include target tissue the photons or electrons are directed at.

In one embodiment, a radiation method comprises pulsing particle generation in a radiation therapy system at a periodic rate, accelerating particles resulting from the pulsing particle generation, wherein the particles are accelerated in a beam, and directing the particles in the beam at a target. The pulsing characteristics can be compatible with ultra high dose rates rate of at least 20 Gy/second. The pulsing particle generation can include pulsing a laser beam and exciting a target with the resulting pulsed laser beam. The pulsing particle generation can include switching on and off the particle generation in accordance with gating controls. In one exemplary implementation, the pulsing particle generation has high fidelity characteristics. In one embodiment, the pulsing particle generation is compatible with FLASH radiation therapy. The pulsing particle generation can be pulsed at a rate corresponding to a microwave range. The pulsing particle generation can include generating photons or electrons that are directed at target tissue and can correspond to a prescribed treatment plan.

BRIEF DESCRIPTION OF THE DRAWINGS

The accompanying drawings together with the description are incorporated in and form a part of this specification. They illustrate exemplary embodiments and explain exemplary principles of the disclosure. They are not intended to limit the present invention to the particular implementations illustrated therein. The drawings are not to scale unless otherwise specifically indicated.

DETAILED DESCRIPTION OF THE INVENTION

Reference will now be made in detail to the preferred embodiments of the invention, examples of which are illustrated in the accompanying drawings. While the invention will be described in conjunction with the various embodiments, it will be understood that they are not intended to limit the invention to the various embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one ordinarily skilled in the art that the present invention may be practiced without these specific details. In other instances, well known methods, procedures, components, and circuits have not been described in detail as not to unnecessarily obscure aspects of the current invention.

Presented systems and methods facilitate efficient and effective control of photon beam generation. In some embodiments, particle beam generation control facilitates ultra high radiation dose rates with high fidelity delivery. The systems and methods are compatible with pulse width modulation. In some exemplary implementations, timing control resolution is configured to facilitate delivery fidelity approaching intra-pulse and micro-bunch levels. A microbunch level can correspond to individual bunches per radio frequency cycle in a pulse width. The radio frequency can be in the microwave range. In some exemplary implementations, a presented system and method can be utilized in FLASH radiation therapy applications. The systems and methods are also compatible with multiple field treatment approaches and can enable dose delivery for each faction/field to be effectively controlled.

Figure 1:
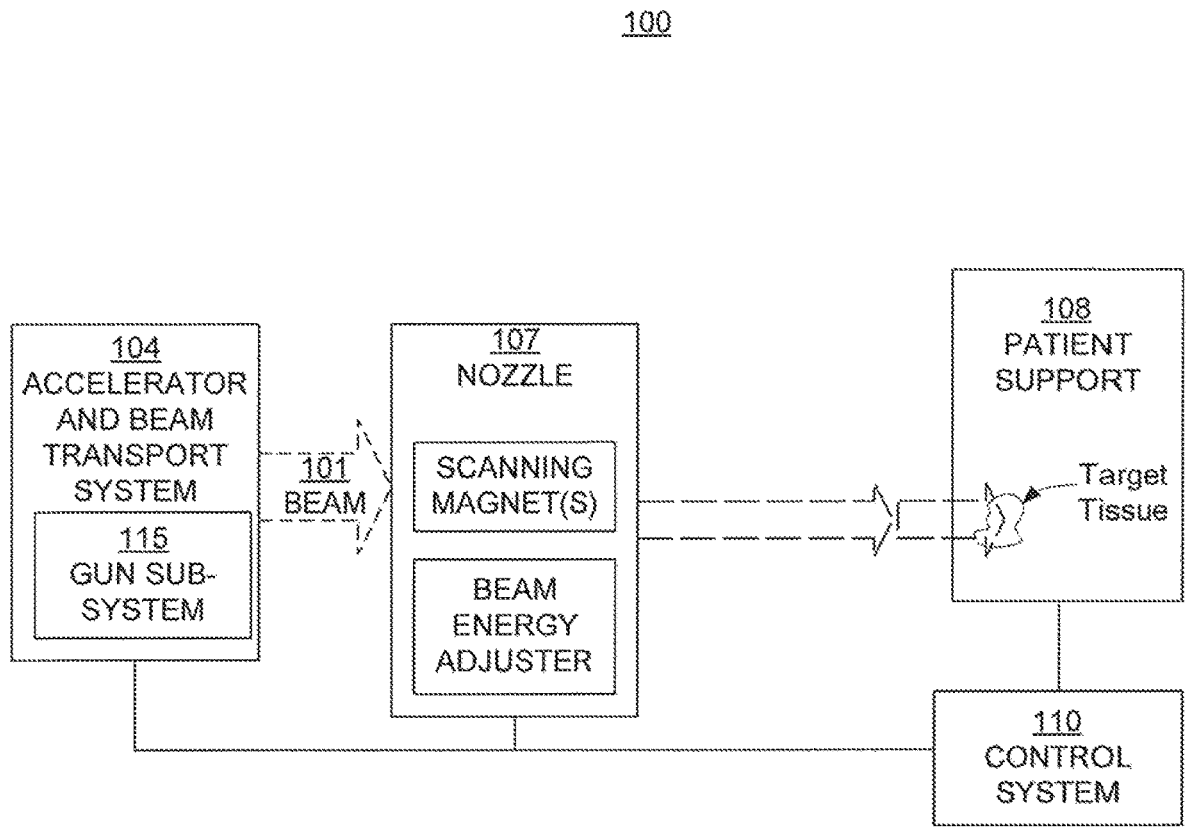
FIG. 1 is a block diagram of an exemplary radiation system in accordance with some embodiments.

FIG. 1 is a block diagram of an exemplary radiation therapy system 100 in accordance with some embodiments. Radiation therapy system 100 includes a beam generation system 104, a nozzle 107, and control system 110. The beam generation system 104 generates and transports a beam of particles (e.g., electrons, protons, neutrons, photons, ions, etc.). In some embodiments, the plurality of particles are travelling in substantially the same direction. In some exemplary implementations, particles traveling in substantially the same direction are included in a beam. The beam can be an atom nuclei beam (e.g., from carbon, helium, lithium, etc.). The beam can be considered a relatively well-defined beam.

In some embodiments, the beam generation system 104 includes a particle accelerator. The particle accelerator can include a liner accelerator. The system is compatible with a variety of accelerators (e.g., a continuous wave beam proton accelerator, an isochronous cyclotron, a pulsed proton accelerator, a synchrocyclotron, a synchrotron, etc.). In some embodiments, the accelerator is capable of relatively continuous wave output and extracts particles with a specified energy. This can provide a high, continuous wave beam current for the high dose rate per shot or treatment application. A shot is the dose delivered in a relatively short period of time along a line segment through the target tissue. Shots can be included in a scan pattern and independently adjusted (e.g., in intensity, in range, etc.) to irradiate a target tissue volume. The accelerator can be a lower power output cyclotron, such as a cyclotron that accelerates particles to the range of 70-300 MeV. The primary particle beam generator may be configured to correlate the time of the secondary photon emission with the particle beam generation (e.g., to further improve signal-to-noise ratio, etc.).

Beam generation system 104 includes gun subsystem 115. Gun subsystem 115 enables high resolution control of particle beam generation. In some embodiments, gun subsystem 115 is compatible with timing control of particle beam generation operations a microwave frequency range. Gun subsystem 115 can be utilized in a radiation therapy system to deliver FLASH radiation therapy. Additional description of gun-subsystems is presented in later portions of this specification.

The beam generation system 104 can include various other components (e.g., dipole magnets, bending magnets, etc.) that direct (e.g., bend, steer, guide, etc.) the beam through the system in a direction toward and into the nozzle 107. The beam generation system 104 may also include components that are used to adjust the beam energy entering the nozzle 107. In some embodiments, sets of quadrupole magnets are located along the beam paths in the beam generation system 104. In some exemplary implementations, the radiation therapy system may include one or more multileaf collimators (MLCs). A MLC leaf can be independently moved back-and-forth by the control system 110 to dynamically shape an aperture through which the beam can pass. The aperture can block or not block portions of the beam and thereby control beam shape and exposure time.

The nozzle 107 can be used to aim the beam toward various locations within an object (e.g., a patient, target tissue, etc.). The object can be located on the supporting device 108 (e.g., a chair, couch, bench, table, etc.) in a treatment room. The nozzle 107 may be mounted on or a part of a fixed, rotating or movable gantry (not shown) so that it can be moved relative to the supporting device 108. The supporting device may also be moveable. In some embodiments, the beam generation system 104 is also mounted on or is a part of the gantry. In some other embodiments, the beam generation system is separate from the gantry. In some exemplary implementations, a separate beam generation system is in communication with the gantry.

In some embodiments, control system 110 receives and directs execution of a prescribed treatment plan. In some exemplary implementations, the control system 110 includes a computer system having a processor, memory, and user interface components (e.g. a keyboard, a mouse, a display, etc.). The control system 110 can control parameters of the beam generation system 104, nozzle 107, and supporting device 108, including parameters such as the energy, intensity, direction, size, and shape of the beam. The control system 110 can receive data regarding operation of the system 100 and control the components according to data it receives. The data can be included in the prescribed treatment plan. In some embodiments, the control system 110 receives information and analyzes the performance and treatment being provided by radiation therapy system 100. The monitor component can measure and track beam current and beam charge, which are used to draw a correlation with the dose rate and dose amount respectively. In some embodiments, control system 110 can direct adjustments to the radiation therapy system 100 bases upon the analysis of dose and dose rate.

As noted above, the particle beam entering the nozzle 107 can have a specified energy and the nozzle 107 includes one or more range shifting and modulating components that affect the energy of the beam. In some embodiments, the nozzle 107 includes components such as magnets that control (e.g., steer, guide, deflect, scan, etc.) the beam particles in "X and Y directions" to scan a target tissue volume. The target tissue volume can be in a patient on the supporting device 108. The nozzle 107 can also include a beam energy adjuster that affects the energy of the particle beam. In some exemplary implementations, adjustments in the particle beam energy can be used to control: the range of the beam (e.g., the extent that the beam penetrates target tissue, etc), the dose delivered by the beam, the depth dose curve of the beam, depending on the type of beam. For example, for a proton beam or an ion beam that has a Bragg peak, the beam energy adjuster can control the location of the Bragg peak in the target tissue. The beam energy adjuster can include various components (e.g., range modulators, range shifters, etc.). The beam system 104 may also include components that are used to adjust the beam energy entering the nozzle 107.

Radiation therapy system 100 can be utilized for high dose rate treatments. Some treatment approaches include ultra-high dose rate treatment or modality referred to as FLASH radiotherapy. Therapeutic windows associated with FLASH therapy often enable reduced normal tissue toxicity while maintaining cancerous tissue tumor control. In some exemplary implementations, the FLASH radiotherapy dose rate can be at least 4 Gray (Gy) in less than one second and as much as 20 Gy or 40 Gy in less than a second. In some exemplary implementations, the FLASH radiotherapy dose rate can be more than 40 Gy in less than one second. The radiation therapy systems and methods are also compatible with multiple field treatment approaches in which different fields are associated with a particular treatment trajectory and a dose per field that is a portion or fraction of a total dose delivery.

Figure 2:
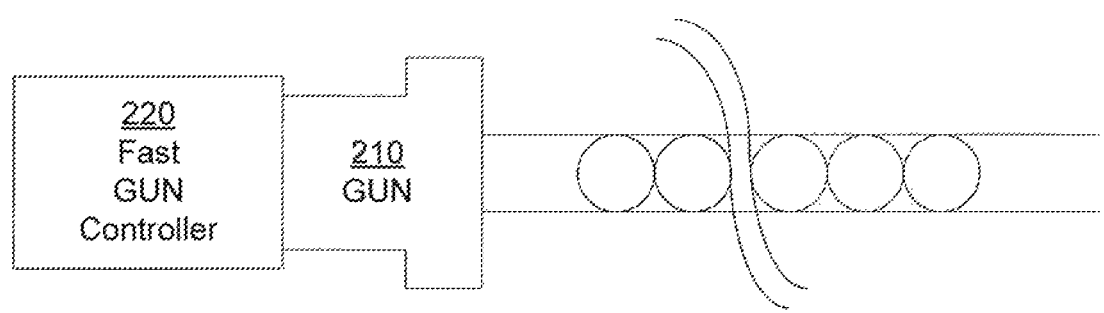
FIG. 2 is a block diagram of a gun subsystem in accordance with some embodiments.

FIG. 2 is a block diagram of a gun subsystem 200 in accordance with some embodiments. Gun subsystem is similar to gun subsystem 115 and can be utilized in a radiation therapy system to deliver FLASH radiation therapy. Gun subsystem 200 includes gun control component 210 and gun 220. Gun 220 generates a particle beam. It is appreciated that gun 220 can be a variety of different gun types. Gun control component 210 controls the gun particle beam generation characteristics, including particle beam fidelity characteristics.

Particle beam fidelity can facilitate utilization of various treatment features. The treatment features or characteristics can include high dose rates, multiple field treatment plans, Intensity Modulated Radio Therapy (IMRT), and so on. High dose rate approaches can facilitate delivery of a prescribed dose very rapidly, thereby reducing the radiation exposure time window and opportunity for undesirable movement of the target tissue. Faster delivery can also reduce discomfort and inconvenience to a patient. Multiple field treatment plans can be used in which different fields are associated with a particular treatment trajectory and a dose per field that is a portion or fraction of a total dose delivery. Delivering a fraction of a dose per field typically results in a reduced exposure time interval per field treatment. It is appreciated that a number of treatment plans can be associated with fine or very small radiation exposure timing intervals. Applying multiple treatment approaches together (e.g., ultra high dose rate in multiple fields) can result in radiation exposure windows being very small (e.g., a fraction of a fraction of a second, etc.).

Gun control component 210 can facilitate particle beam generation that has timing resolutions and fidelity characteristics compatible with very short radiation exposure intervals. In some embodiments, a gun subsystem is configured to control particle beam generation timing intervals associated with delivery of a field dose fraction at a high dose rate. In some exemplary implementations, a gun-subsystem can control particle beam generation in accordance with pulse width modulation techniques. In some embodiments, a dose can be delivered over a few pulses depending on pulse width and pulsed radio frequency fields (PRF).

In some embodiments, resolution control of particle beam generation can enable dose delivery at intra-pulse and micro-bunch levels. In some exemplary implementations, a micro-bunch level includes individual bunches per each 3 GHz RF cycle within a 5 to 15 μsec pulse-width. The ability to control dose delivery approaching the bunch level can improve resolution to approximately $4.4 \times 10^{-6}$ cGy/bunch. It is appreciated that this resolution may be more than needed in some treatment plans. In some exemplary implementations, the resolution control facilitates approximately one percent control on the dose delivery. The treatment or dose resolution can be useful when implemented to arc treatments. It is appreciated a gun subsystem can include various implementations.

In some embodiments, the system can deliver 20 Gy/sec at 100 cm. The beam energy can be 20 MeV at a beam power of 10 kW with an average beam current of 0.5 mA and a peak beam current of 33 mA. It is appreciated that these values are exemplary. In some exemplary implementations, a system and method can operate within a range of these values (e.g., within 1%, within 5%, 5% to 20%, etc.).

Figure 3:
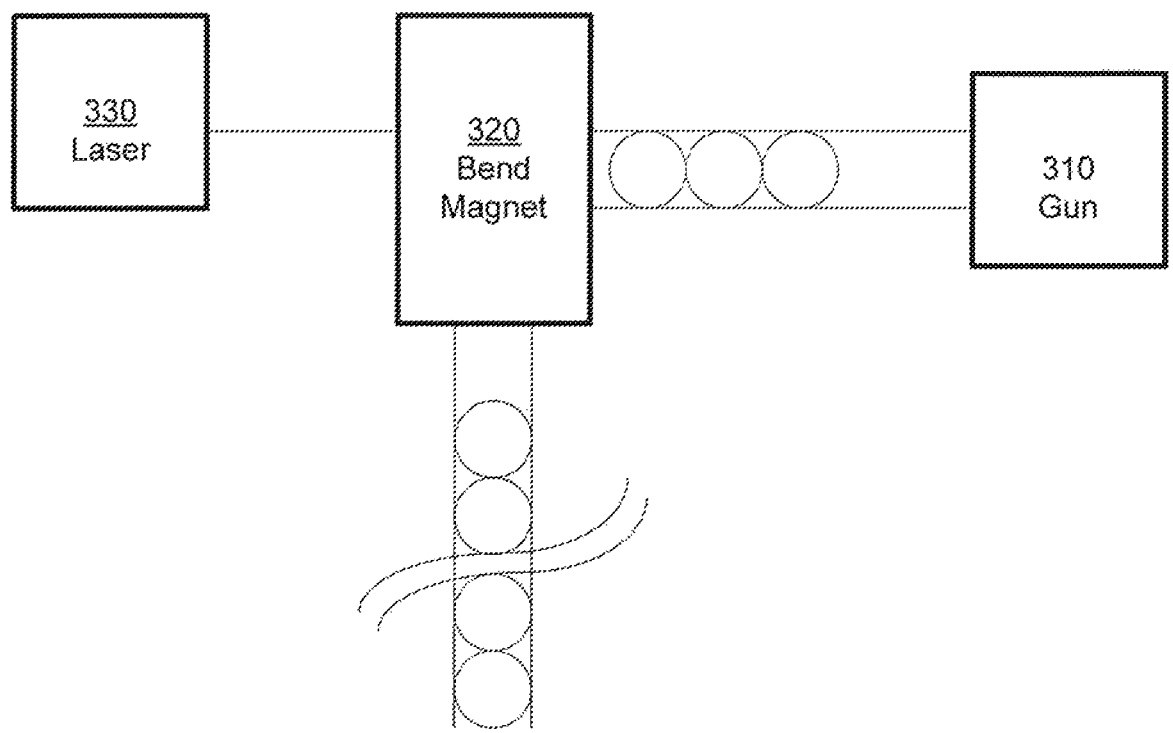
FIG. 3 is a block diagram of an exemplary laser controlled gun subsystem in accordance with some embodiments.

FIG. 3 is a block diagram of an exemplary laser controlled gun subsystem 300 in accordance with some embodiments. Gun subsystem 300 includes photocathode gun 310, a bend magnet 320, and laser component 330. Gun 301 includes a photocathode gun operable to emit electrons when excited by the laser. Gun 301 can be an integral part of a linear accelerator. The linear accelerator can have a first section and a second section with a bend component coupled between the sections. The bend component 320 is operable to bend the electrons accelerated by the gun-subsystem and the first linear accelerator section. The bend component can include a bend magnet that influences or directs the electrons through the bend. In some embodiments, the bend component 310 is configured to provide a line-of-site path for an exciting laser from laser component 330 to a photo-cathode included in gun component 310. The bent particle beam is directed into a second linear accelerator to accelerate the particle beam to its final energy. In some embodiments, the particle beam energy can be adjusted after the second linear accelerator.

The laser component 330 is operable to control "gating" or switching on and off of the electron emission from the gun. In some embodiments, a 5 usec pulse corresponds to ~15K e-bunches, which can be turned on and off utilizing the on/off function of the photocathode injector to control the dose output approximating resolution of dose per bunch. In some embodiments, the laser is pulsed at frequencies in a microwave range. In some exemplary implementations, the oscillation is in the 3 GHz range. In some embodiments, the laser is pulsed away from the rise and fall transient parts of a waveform.

Figure 4:
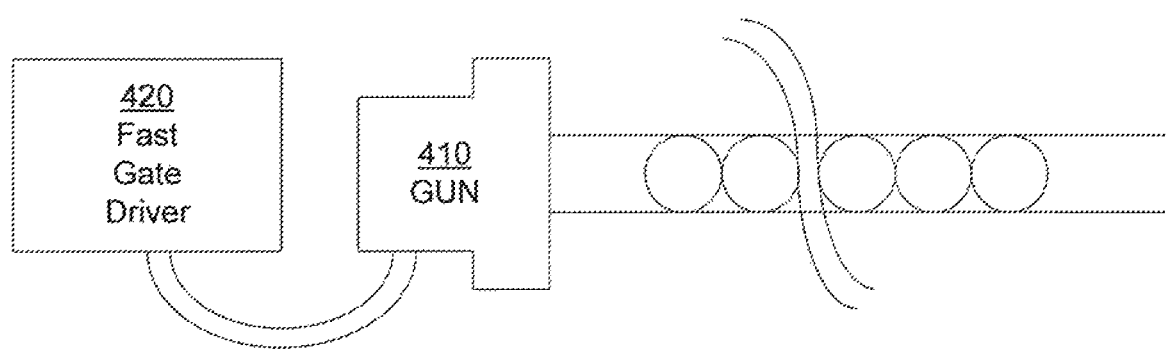
FIG. 4 is a block diagram of another exemplary driver controlled gun subsystem in accordance with some embodiments.

FIG. 4 is a block diagram of an exemplary driver controlled gun subsystem 400 in accordance with some embodiments. Gun subsystem 400 includes a gridded gun 410 and fast gun driver component 420. Fast gun driver component 420 is capable of gating a grid on and off as quickly as 333 psec, which in turn enables bunch gating resolution. In some embodiments, fast gun driver component 420 facilitates intra-pulse dose-delivery control.

Figure 5:
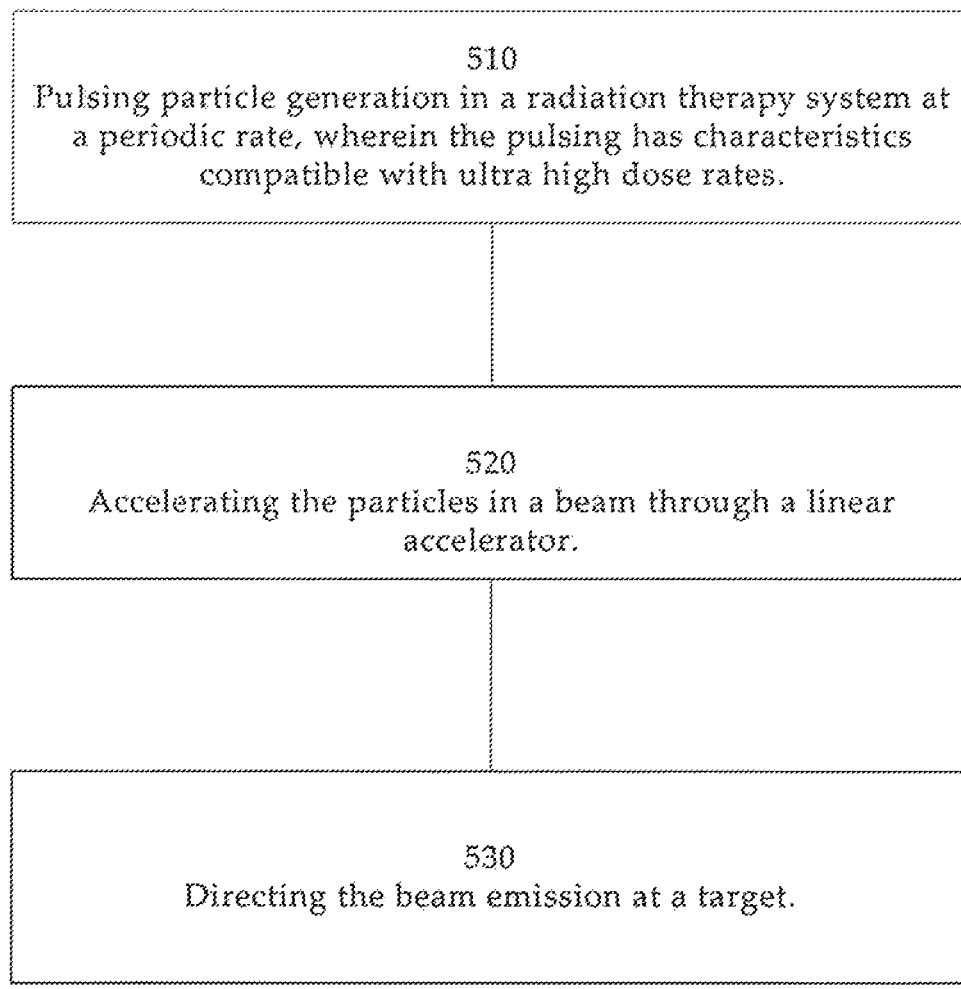
FIG. 5 is a block diagram of a particle beam generation method in accordance with some embodiments.

FIG. 5 is a block diagram of a particle beam generation method 500 in accordance with some embodiments.

In block 510, particle generation in a radiation therapy system is pulsed at a periodic rate. The pulsing can be in a microwave range. In some embodiments the pulsing has characteristics compatible with ultra high dose rates. The pulsing can have high fidelity characteristics.

In block 520, the particles are accelerated in a beam through a linear accelerator. In some embodiments, the linear accelerator includes a portion that accelerates the particles. In some exemplary implementations, the linear accelerator includes a portion that decelerates the particles.

In block 530, the beam emission is directed at a target. In some embodiments, the particle beam includes electrons that are directed at a target that emits photons and the photons are directed at target tissue. In some exemplary implementations, the particle beam includes electrons that are directed at the target tissue.

It is appreciated that in addition to medical applications, fast gun control may also have other applications such as industrial applications where high dose rates facilitate various characteristics (e.g., radiation hardening, cross-linking, etc.)

Thus, the presented systems and methods facilitate efficient and effective radiation beam generation. In some embodiments, a pulse width high dose rate control system and method enables improved fidelity over coarser traditional gun control pulse dropping and pulse servoing approaches.

Some portions of the detailed descriptions are presented in terms of procedures, logic blocks, processing, and other symbolic representations of operations on data bits within a computer memory. These descriptions and representations are the means generally used by those skilled in data processing arts to effectively convey the substance of their work to others skilled in the art. A procedure, logic block, process, etc., is here, and generally, conceived to be a self-consistent sequence of steps or instructions leading to a desired result. The steps include physical manipulations of physical quantities. Usually, though not necessarily, these quantities take the form of electrical, magnetic, optical, or quantum signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are associated with the appropriate physical quantities and are merely convenient labels applied to these quantities. Unless specifically stated otherwise as apparent from the following discussions, it is appreciated that throughout the present application, discussions utilizing terms such as "processing", "computing", "calculating", "determining", "displaying" or the like, refer to the action and processes of a computer system, or similar processing device (e.g., an electrical, optical or quantum computing device) that manipulates and transforms data represented as physical (e.g., electronic) quantities. The terms refer to actions and processes of the processing devices that manipulate or transform physical quantities within a computer system's component (e.g., registers, memories, other such information storage, transmission or display devices, etc.) into other data similarly represented as physical quantities within other components.

The foregoing descriptions of various specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as suited to the particular use contemplated. It is intended that the scope of the invention be defined by the Claims appended hereto and their equivalents. The listing of steps within method claims do not imply any particular order to performing the steps, unless explicitly stated in the claim.

What is claimed:

1. A radiation method comprising:
generating a particle beam;
controlling generation characteristics of the particle beam, including controlling pulsing or gating on and off of the particle beam, so that the particle beam has fidelity characteristics according to data in a treatment plan; and
accelerating particles in the particle beam, wherein the particle beam includes electrons that are directed at a target that emits photons and the photons are directed at target tissue in accordance with the treatment plan, wherein the treatment plan includes a photon dose rate of at least 20 Gy/second.

2. The radiation method of claim 1, wherein resolution control of the particle beam generation is configured to provide photon dose delivery at an intra-pulse level.

3. The radiation method of claim 1, wherein resolution control of the particle beam generation is configured to provide photon dose delivery at a micro-bunch level.

4. The radiation method of claim 3, wherein the micro-bunch level includes individual bunches per each 3 GHz frequency cycle within a 5 to 15 μsec pulse-width.

5. The radiation method of claim 3, wherein the generation characteristics of the particle beam includes configuring particles in electron bunches with a bunch level resolution of approximately $4.4 \times 10^{\wedge}-6$cGy/bunch, plus or minus 5 percent.

6. The radiation method of claim 1, wherein in a 5 μsec pulse there are plus or minus 5 percent of 15,000 pulses or on and off operations/bunch to control a dose output corresponding to a resolution of dose per bunch.

7. The radiation method of claim 1, wherein the pulsing or gating is initiated within a middle portion of a pulse reducing energy spread associated with transients and rise/fall times of the pulsing or gating on and off of the particle beam.

8. The radiation method of claim 1, wherein the pulsing or gating occur at a rate that corresponds to a bunch resolution, wherein the bunch resolution defines an amount of electrons in a bunch and an amount of particles in the particle beam corresponds to the bunch resolution.

9. The radiation method of claim 1, wherein gating is at 333 psec.

10. A radiation method comprising:
pulsing particle generation in a radiation therapy system at a periodic rate, wherein the pulsing comprises switching a particle generator on and off in accordance with gating controls;
accelerating particles resulting from the pulsing particle generation, wherein the particles are accelerated in a beam;

wherein the pulsing particle generation has high fidelity characteristics; and directing the particles in the beam at a target that emits photons with ultra-high dose rates of at least 20 Gy/second.

11. A radiation method of claim 10, wherein the pulsing particle generation comprises:

pulsing a laser beam; and exciting the target with the resulting pulsed laser beam.

12. A radiation method of claim 10, wherein the pulsing particle generation is pulsed at a rate corresponding to a microwave range.

13. A radiation method of claim 10, wherein the pulsing particle generation is directed to providing photon radiation in accordance with a prescribed treatment plan.

\* \* \* \* \*